(12) United States Patent
Su et al.

(10) Patent No.: US 9,124,031 B2
(45) Date of Patent: Sep. 1, 2015

(54) PLUGGABLE SELF LOCKING CONNECTOR

(71) Applicant: NEXTRONICS ENGINEERING CORP., New Taipei (TW)

(72) Inventors: Hou-An Su, Keelung (TW); Hai-Wen Yang, Baoji (CN); Xin-Chao Xiao, Lianyuan (CN)

(73) Assignee: NEXTRONICS ENGINEERING CORP., New Taipei (TW)

( * ) Notice: Subject to any disclaimer, the term of this patent is extended or adjusted under 35 U.S.C. 154(b) by 73 days.

(21) Appl. No.: 14/154,304

(22) Filed: Jan. 14, 2014

(65) Prior Publication Data

US 2014/0235085 A1  Aug. 21, 2014

(30) Foreign Application Priority Data

Feb. 18, 2013 (CN) ...................... 2013 2 0075981 U

(51) Int. Cl.
*H01R 13/506* (2006.01)
*H01R 13/627* (2006.01)
*H01R 13/633* (2006.01)

(52) U.S. Cl.
CPC .......... *H01R 13/6277* (2013.01); *H01R 13/506* (2013.01); *H01R 13/6273* (2013.01); *H01R 13/633* (2013.01)

(58) Field of Classification Search
USPC ......... 439/352, 133, 346–348, 686, 695, 701, 439/712, 713, 724, 879, 345, 660
See application file for complete search history.

(56) References Cited

U.S. PATENT DOCUMENTS

| | | | | |
|---|---|---|---|---|
| 3,721,939 A * | 3/1973 | Paugh | ........................... | 439/354 |
| 5,288,243 A * | 2/1994 | Mergless | ........................ | 439/357 |
| 6,464,526 B1 * | 10/2002 | Seufert et al. | .................. | 439/352 |
| 6,508,669 B2 * | 1/2003 | Wang | ............................ | 439/598 |
| 7,758,370 B1 * | 7/2010 | Flaherty | ......................... | 439/352 |
| 7,938,670 B2 * | 5/2011 | Nania et al. | .................... | 439/354 |
| 2002/0182924 A1 * | 12/2002 | Mo | ................................ | 439/358 |

* cited by examiner

*Primary Examiner* — Abdullah Riyami
*Assistant Examiner* — Harshad Patel
(74) *Attorney, Agent, or Firm* — Li & Cai Intellectual Property (USA) Office

(57) ABSTRACT

A pluggable self locking connector includes a socket having a socket case and a plug having a plug shell and a snap fit portion coupled thereto. The socket case is formed with a depression on the inner wall. The outer wall of the snap fit portion is formed with a deformable resilient rib and a bump. The plug shell is formed with an opening for receiving the resilient rib and a resilient latch corresponding to the bump. The front end of the plug shell has a resilient positioning member. When the socket and plug mate, the resilient rib slides into the depression. When the socket and the plug separate, the resilient rib is confined within the depression and the resilient latch and the bump are engaged. The front end of the snap fit portion presses the resilient positioning member and the resilient positioning member is partially exposed.

12 Claims, 11 Drawing Sheets

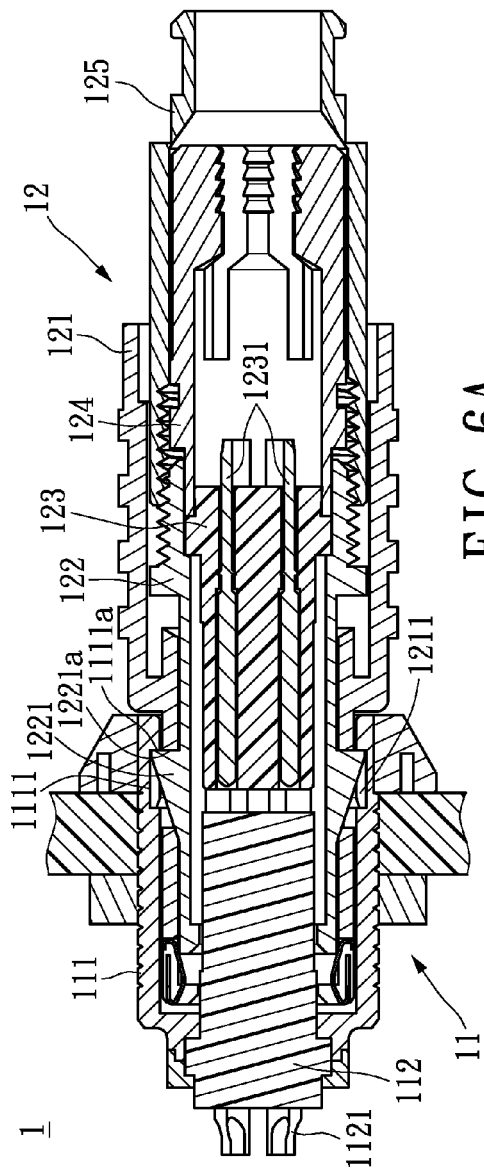
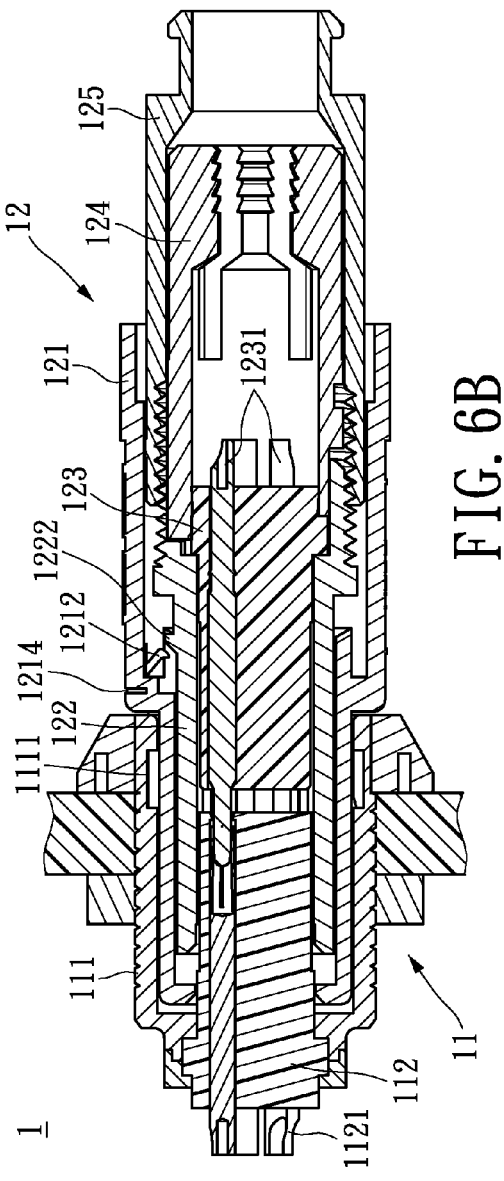
FIG. 6A
FIG. 6B

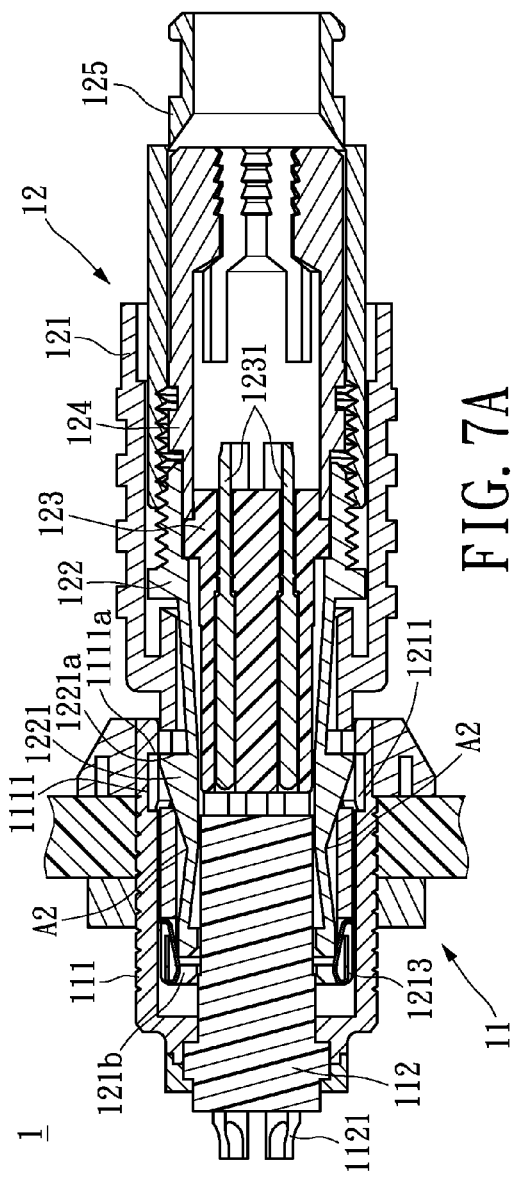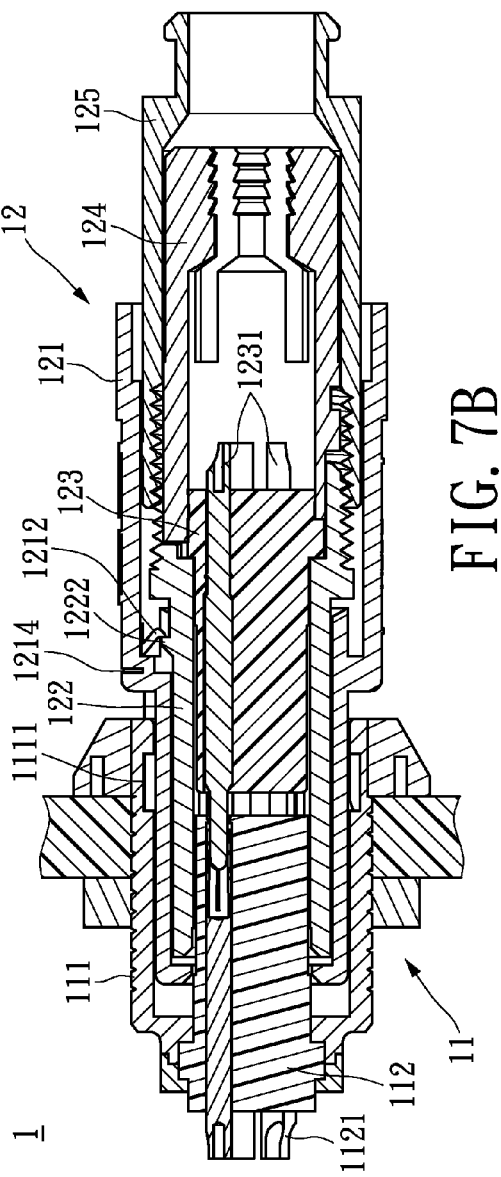

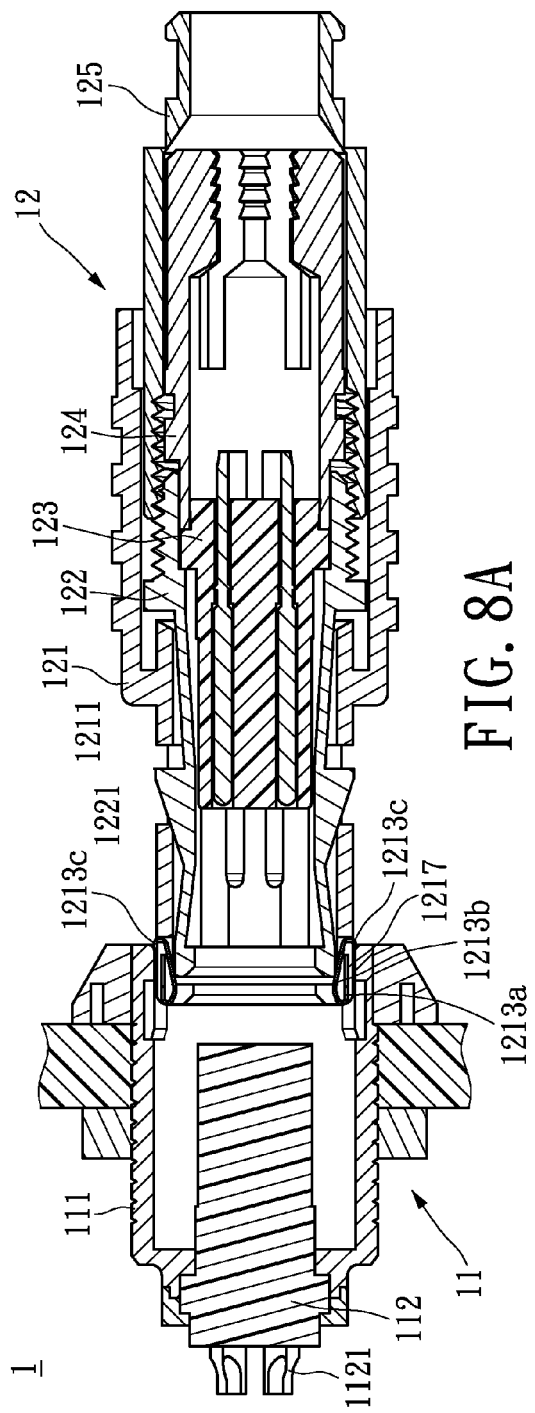
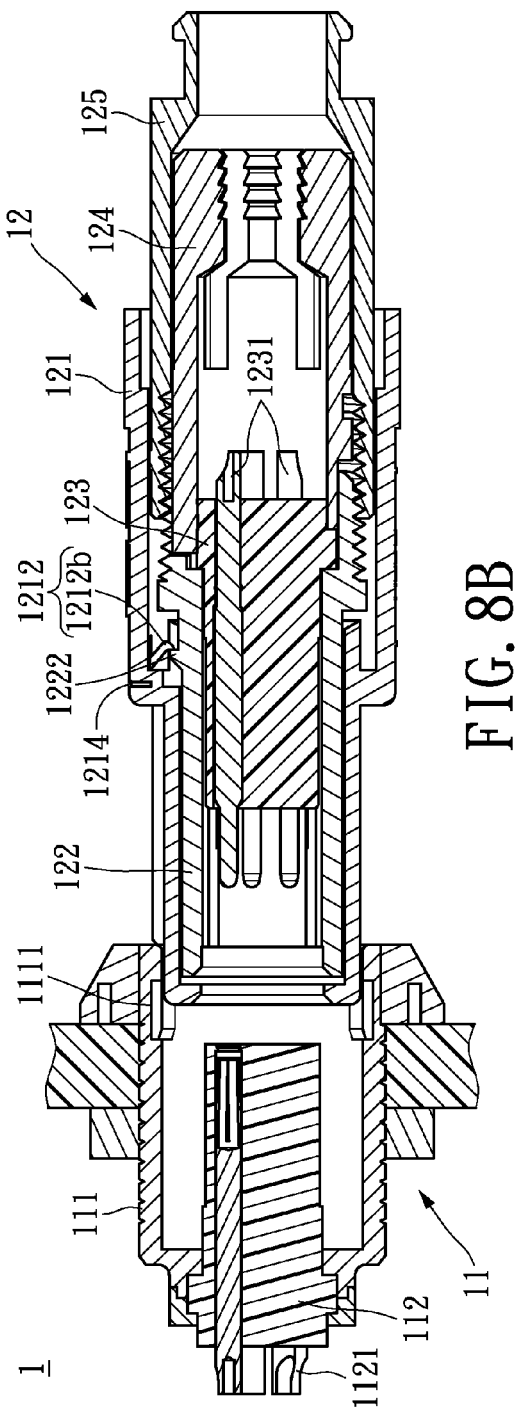
FIG. 8A
FIG. 8B

PLUGGABLE SELF LOCKING CONNECTOR

BACKGROUND

1. Field of the Invention

The instant disclosure relates to a connector; in particular, to a self locking connector for preventing repeated plugging/drawing, applicable to disposable medical device.

2. Description of Related Art

In the case of highly infectious diseases (e.g., severe acute respiratory syndrome, smallpox, tuberculosis and the like), although relevant regulation has been applied, the front line paramedics are still at risk to bacterial or viral infection because of unsuitable protection. This may further lead to the loss of paramedics. Paramedics may feel physically and mentally unsecure when conducting the treatment. If a paramedic is infected and continues his or her routine, the disease may spread among any people within close contact.

However, the conventional connector used in medical device (e.g., monitoring device, imaging device and the like) can be a tubular locking connector or a tubular re-pluggable connector. The tubular locking connector cannot be fastly detached in emergency. Also, the tubular locking connector may easily fall off upon impact, and the signal transmission is interrupted. The conventional connector cannot satisfy the high standard in the case of highly infectious diseases; especially in the operation room, surgery and the like. Thus, large amount of time and labor is investigated in sterilizing the medical device to avoid secondary infection. The cost of human and medical source is considerable.

To address the above issues, the inventor strives via associated experience and research to present the instant disclosure, which can effectively improve the limitation described above.

SUMMARY OF THE INVENTION

The instant disclosure provides a pluggable self locking connector for preventing plug reentry to the socket by the design of the plug shell and the snap fit portion.

The pluggable self locking connector includes a socket including a socket case. The socket case includes a plastic socket core having a plurality of socket pins in the interior and a depression is formed on the inner wall of the socket case. The pluggable self locking connector also includes a plug including a plug shell and a snap fit portion slidably coupled to the plug shell. The plug is coupled to the socket case and connected thereto, and the snap fit portion has a plastic plug core formed with a plurality of plug pins corresponding to the socket pins. The outer wall of the snap fit portion is formed with at least one deformable resilient rib and a bump. The plug shell is formed with an opening for receiving the resilient rib and a resilient latch corresponding to the bump. The front end of the plug shell has at lest one resilient positioning member.

In short, the depression of the socket case and the resilient rib of the snap fit portion are engaged such that the plug is firmly attached to the socket to avoid signal transmission interruption. In addition, the socket case confines the snap fit portion and the socket case such that the resilient latch of the plug shell and the bump of the snap fit portion are tightly engaged. Also, the resilient positioning member prevents the reentry of the plug by the interaction with the socket case.

In order to further understand the instant disclosure, the following embodiments are provided along with illustrations to facilitate the appreciation of the instant disclosure; however, the appended drawings are merely provided for reference and illustration, without any intention to be used for limiting the scope of the instant disclosure.

BRIEF DESCRIPTION OF THE DRAWINGS

FIG. 6A is a cross-sectional view along X axis showing a pluggable self locking connector of the instant disclosure being locked after insertion;

FIG. 6B is a cross-sectional view along Y axis showing a pluggable self locking connector of the instant disclosure being locked after insertion;

FIG. 7A is a cross-sectional view along X axis showing a pluggable self locking connector of the instant disclosure being withdrawn after insertion;

FIG. 7B is a cross-sectional view along Y axis showing a pluggable self locking connector of the instant disclosure being withdrawn after insertion;

FIG. 8A is a cross-sectional view along X axis showing a pluggable self locking connector of the instant disclosure after second insertion;

FIG. 8B is a cross-sectional view along Y axis showing a pluggable self locking connector of the instant disclosure after second insertion;

DETAILED DESCRIPTION OF THE PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings. The instant disclosure provides a pluggable self locking connector 1, which satisfies water proof IP50. The connector 1 is a disposable tubular multi-core connector for surgical use. The connector 1 may also be a tubular multi-core connector which satisfies water proof IP50 and IP68 for precision medical instrument and the instant disclosure is not limited thereto. In other words, the pluggable self locking connector 1 can be implemented to other machines.

Figure 1:
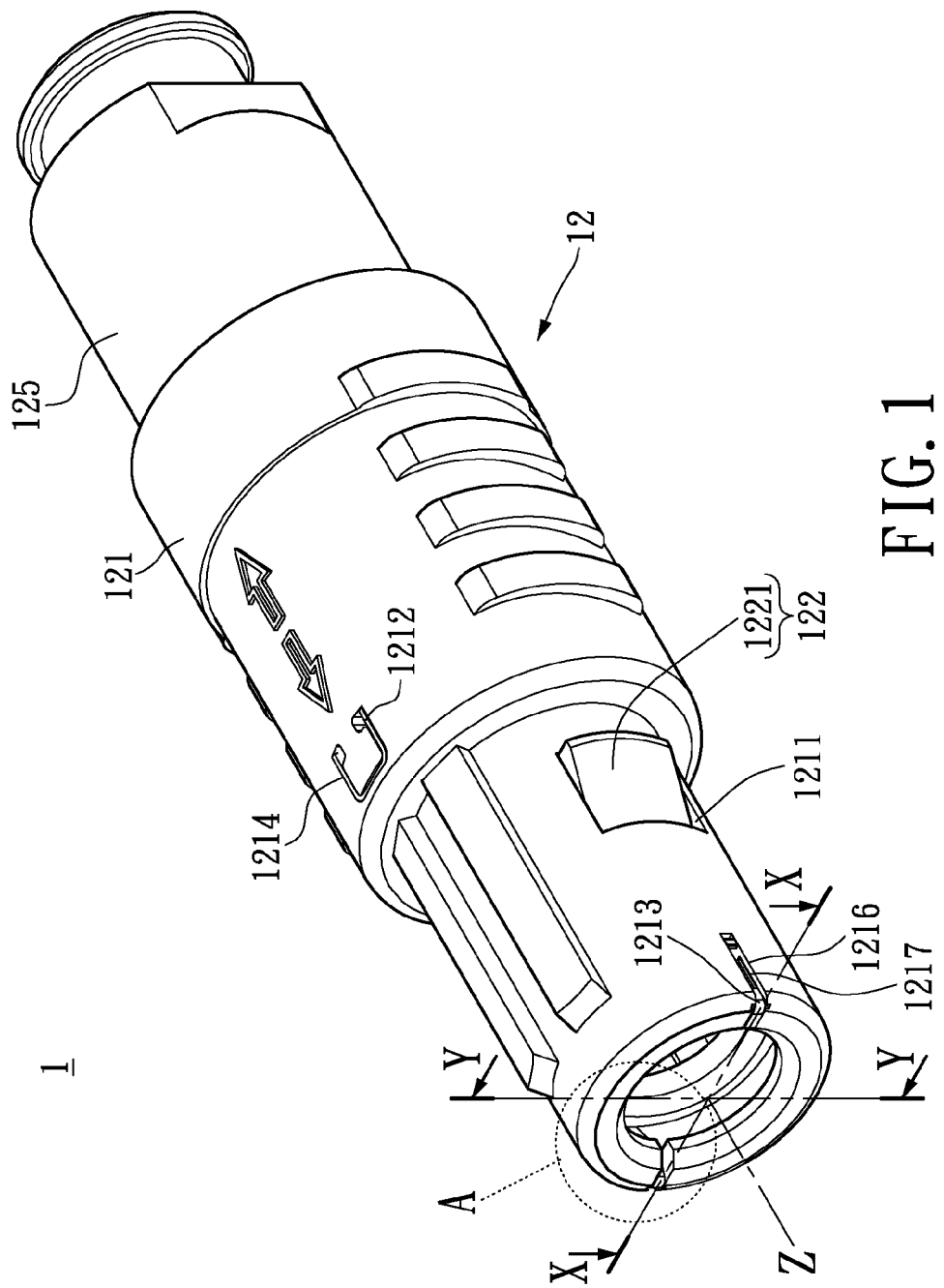
FIG. 1 is a perspective view of an assembled pluggable self locking connector of the instant disclosure.
Figure 2:
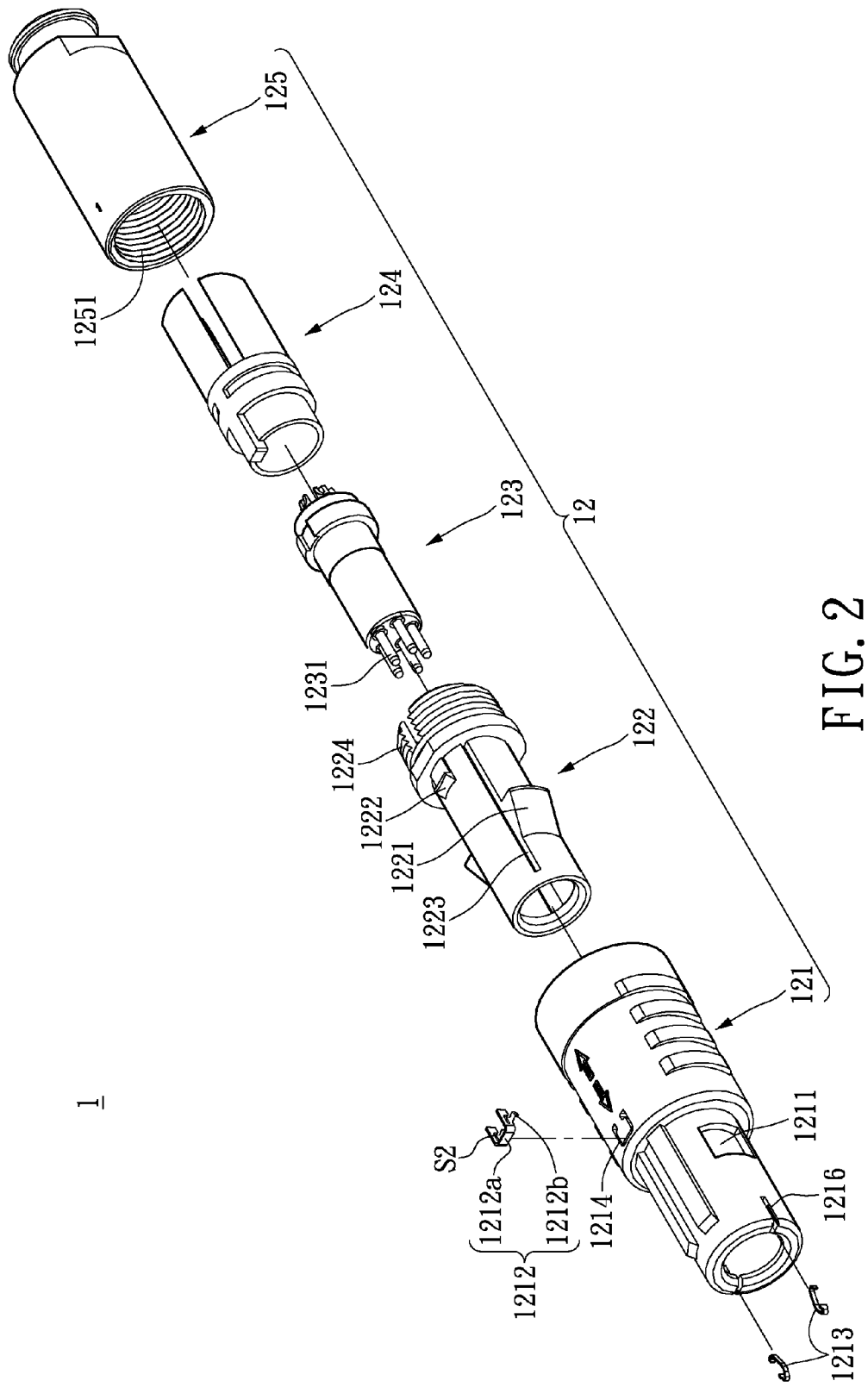
FIG. 2 is an exploded perspective view of a pluggable self locking connector of the instant disclosure.

Please refer to FIGS. 1 to 8B. As shown in FIGS. 1, 2 and 4A, the pluggable self locking connector 1 includes a socket 11 (shown in FIG. 4A) and a plug 12. The socket 11 can mate with the plug 12 (as shown in FIG. 6A), and the electricity or electronic signal is transmitted therebewteen. The socket 11 includes a socket case 111, and the interior of the socket 111 has a plastic socket core 112. The plug 12 includes a plug shell 121, and the outer face of the plug shell 121 has a snap-fit portion 122. The snap-fit portion 122 has a plastic plug core 123. The plastic socket core 112 has a plurality of socket pins 1121 electrically connected to plug pins 1231 of the plastic plug core 123 when mating.

Figure 4A:
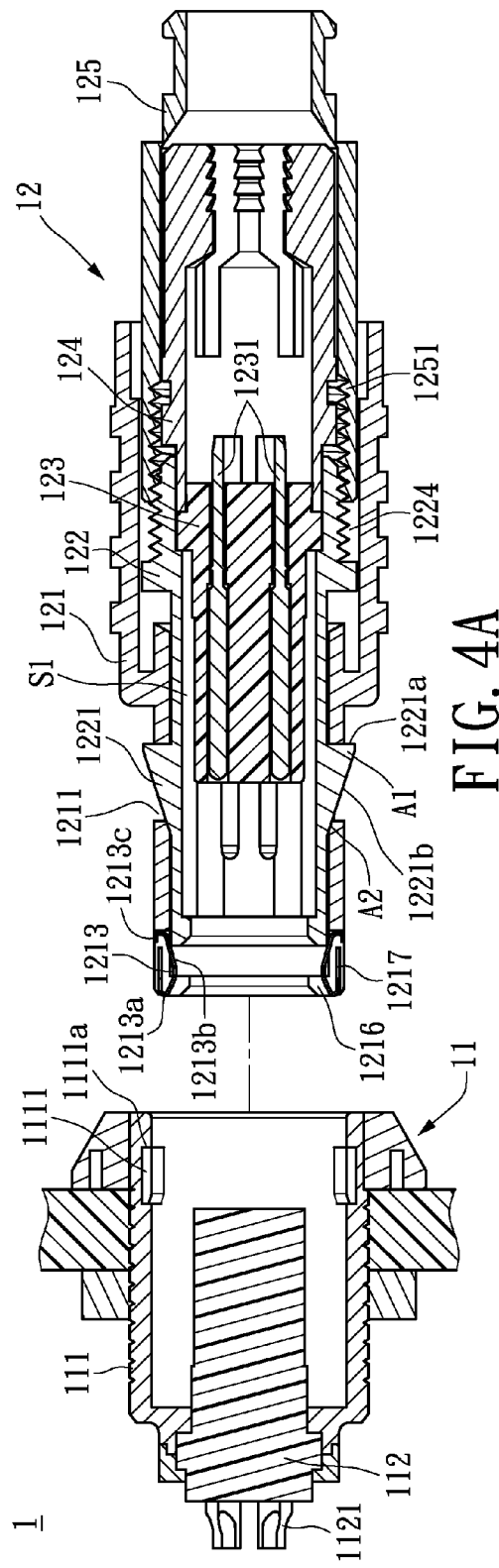
FIG. 4A is a cross-sectional view along X axis showing an unassembled pluggable self locking connector of the instant disclosure.
Figure 4B:
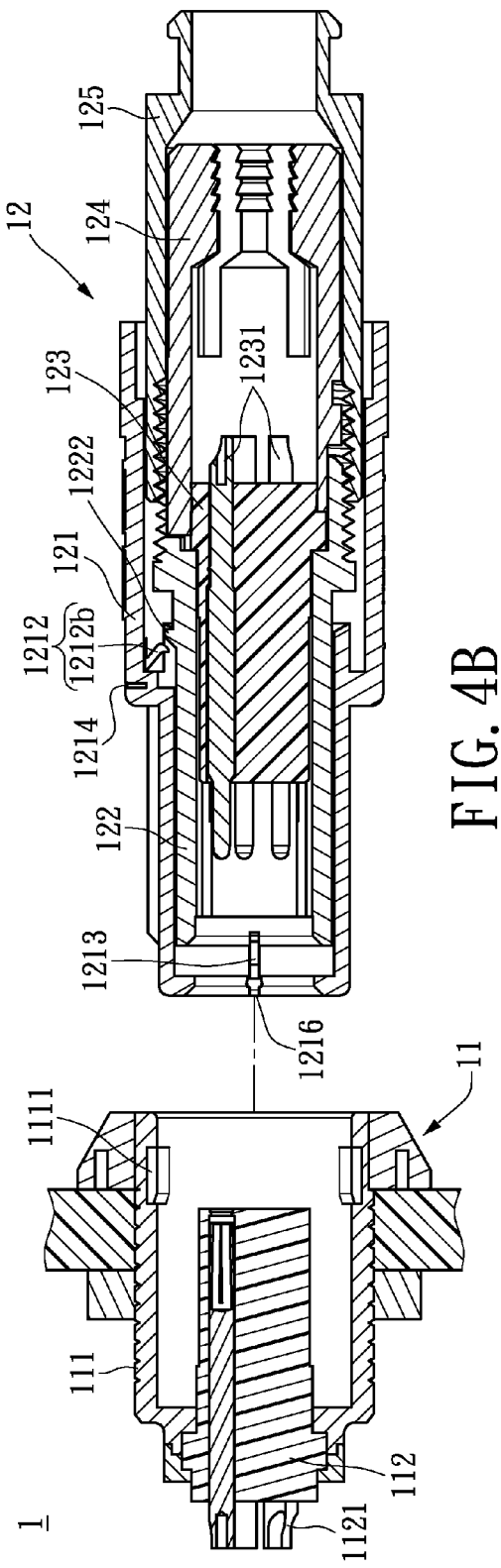
FIG. 4B is a cross-sectional view along Y axis showing an unassembled pluggable self locking connector of the instant disclosure.

As shown in FIGS. 1 and 4A, the outer face of the snap-fit portion 122 has at least one resilient rib 1221. The outer face is also formed with an opening 1211 which receives the resilient rib 1221 upon sliding in. The resilient rib 1221 projects and is exposed from the opening 1211. Additionally, the inner wall of the socket case 111 is formed with a depression 1111 for receiving the resilient rib 1221. When the socket 11 and the plug 12 mate, the resilient rib 1221 of the snap-fit portion 122 rests in the depression 1111 of the socket case 111 (shown in FIG. 6A). Therefore, the plug 12 is firmly secured on the socket 11, and at the same time the signal transmission is also carefully maintained. Furthermore, as shown in FIGS. 2 and 7B, a bump 1222 is formed on the outer face of the snap-fit portion 122, and the plug shell 121 has a resilient latch 1212 corresponding to the bump 1222. The front end of the plug shell 121 has at least one resilient positioning member 1213 embedded therein. When the plug 12 withdraws from the socket 11, the resilient rib 1221 of the snap-fit portion 122 is confined in the depression 1111 of the socket case 111. In other words, when the plug 12 unplugs from the socket 11, the plug shell 121 moves backwards while the front end of the snap-fit portion 122 presses against the resilient positioning member 1213. As a result, a portion of the plug shell 121 is exposed (shown in FIG. 7A). Meanwhile, the resilient latch 1212 of the socket case 121 abuts the bump 1222 of the snap-fit portion 122 (shown in FIG. 7B) such that the plug shell 121 and the snap-fit portion 122 are fixedly engaged. Hence, the plug shell 121 cannot rejoin with the socket 11 because of the presence of the resilient positioning member 1213 (shown in FIG. 8A). That is, the socket 11 allows only a one-time entry of the plug 12. The plug 12 of the pluggable self locking connector 1 has to be discarded after use and the secondary infection can be effectively avoided.

Referring to FIGS. 2 and 4A, an embodiment of the instant disclosure is further discussed herein. The pluggable self locking connector 1 includes the socket 11 and a plug 12. The plug 12 is formed with a channel going through the centre region (not shown) for accommodating power cables or electronic leads (not shown). The cables and leads are connected to the plug pin 1231 of the plastic plug core 123. The plug 12 connects to the socket 11 by snap fit. The socket case 111 and the plug shell 121 can be made of anti-bacteria metal or plastic materials to adapt in any medical application and the instant disclosure is not limited thereto.

The snap-fit portion 122 is slidably inserted to the interior of the plug shell 121, and the at least one resilient rib 1221 is exposed at the opening 1211 of the plug shell 121. The outer face of the snap-fit portion 122 is formed with a plurality of slits 1223 which attenuates the overall rigidity of the snap-fit portion 122. As a result, the resilient rib 1221 located between two slits 1223 are provided with more flexibility especially in flipping. The number and position of the slits 1223 can vary and the instant disclosure is not limited thereto. For example, two or more than two diagonal slits 1223 (not shown) are formed on the outer face of the snap-fit portion 122. In the instant embodiment, two parallel slits 1223 are formed on the outer face of the snap-fit portion 122, and the resilient rib 1221 is located therebetween. A gap S1 (as shown in FIG. 4A) is formed between the snap-fit portion 122 and the plastic plug core 123. When the socket case 111 presses against the resilient rib 1221, the gap S1 provides a room for the resilient rib 1221 to deform. The length of each slit 1223 affects the flexibility provided to the resilient rib 1221. In the instant embodiment, a pair of resilient ribs 1221 is formed on the opposite sides of the outer face of the snap-fit portion 122 and a pair of openings 1211 is formed on the outer face of the plug shell 121 corresponding to the pair of resilient ribs 1221, such that the snap-fit portion 122 slides in the plug shell 121 and is engaged thereby. The resilient rib 1221 may vary in configuration as long as the snap-fit portion 122 can slide in the plug shell 121 smoothly. The number and shape of the resilient rib 1221 are not restricted by the instant embodiment.

Figure 3:
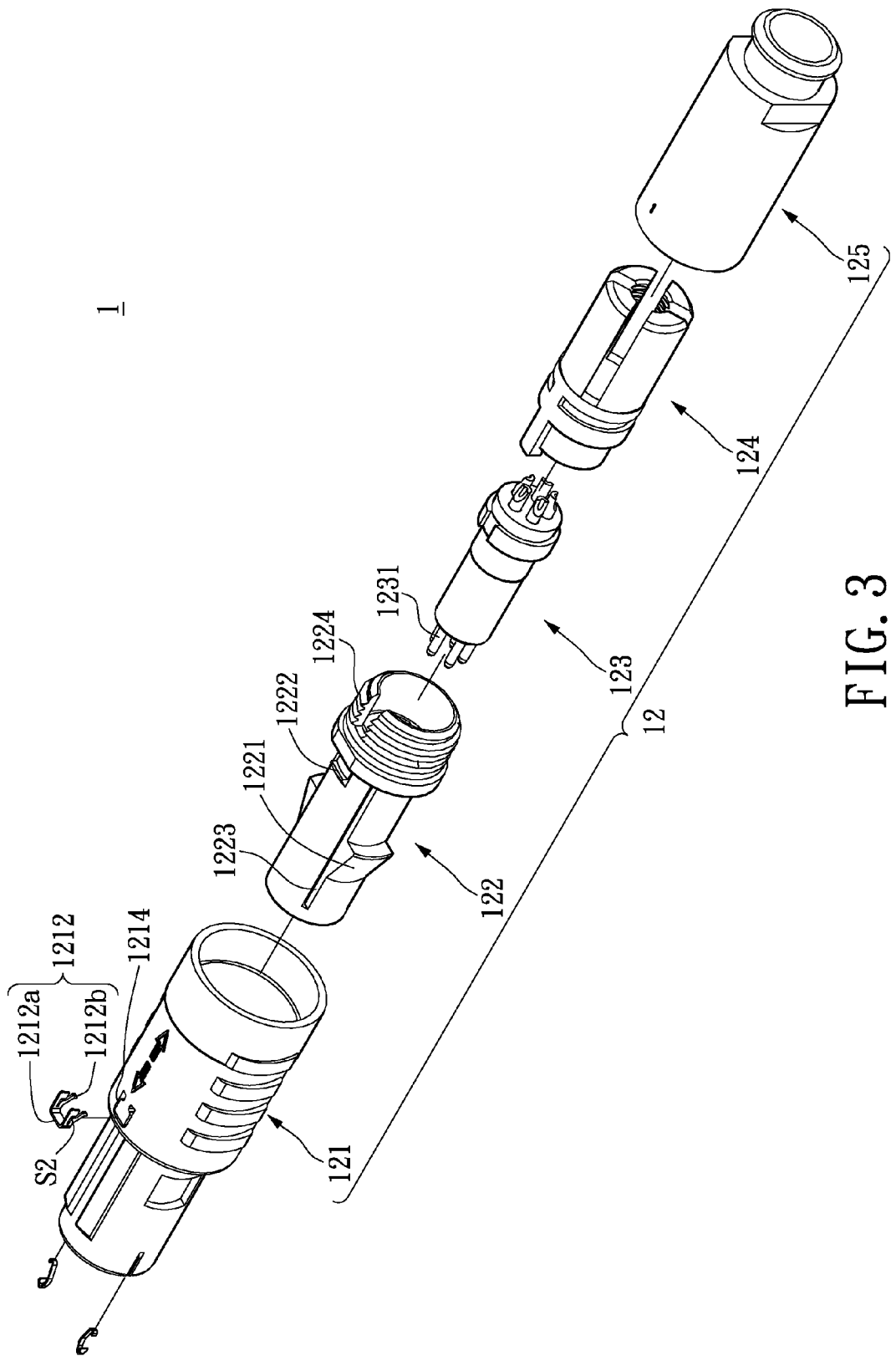
FIG. 3 is another exploded perspective view of a pluggable self locking connector of the instant disclosure.

Referring to FIG. 4A, the inner wall of the socket case 111 is formed with an annular depression 1111. The depression 1111 has a first guiding face 1111$a$, and the resilient rib 1221 of the snap-fit portion 122 has a second guiding face 1221$a$ corresponding to the first guiding face 1111$a$. The guiding faces allow a smooth contact between the resilient rib 1221 and the depression 1111 (as shown in FIGS. 6A to 7B). Furthermore, the guiding faces facilitate an intended relative movement between the snap-fit portion 122 and the plug shell 121. In addition, the resilient rib 1221 has a guiding slope 1221$b$ connected to the second guiding face 1221$a$. The second guiding face 1221$a$ and the guiding slope 1221$b$ meet at a point and form an angle A1. The front end of the guiding slope 1221$b$ is curved to form an arc angle A2. The plug shell 121 can slide along the arc angle A2 and compress the resilient rib 1221. In addition, as shown in FIGS. 2 and 3, the middle portion of the plug shell 121 is formed with a latch slot 1214 for receiving the resilient latch 1212. The resilient latch 1212 has a main body 1212$a$ resembling a horse shoe and a pair of parallel hooks 1212$b$ slantingly extending rearward from the main body 1212$a$. The hooks 1212$b$ are tightly engaged with the bump 1222 of the snap-fit portion 122. The main body 1212$a$ is formed with a pair of trenches S2 for receiving the hooks 1212$b$ when deforming under pressure.

Figure 1A:
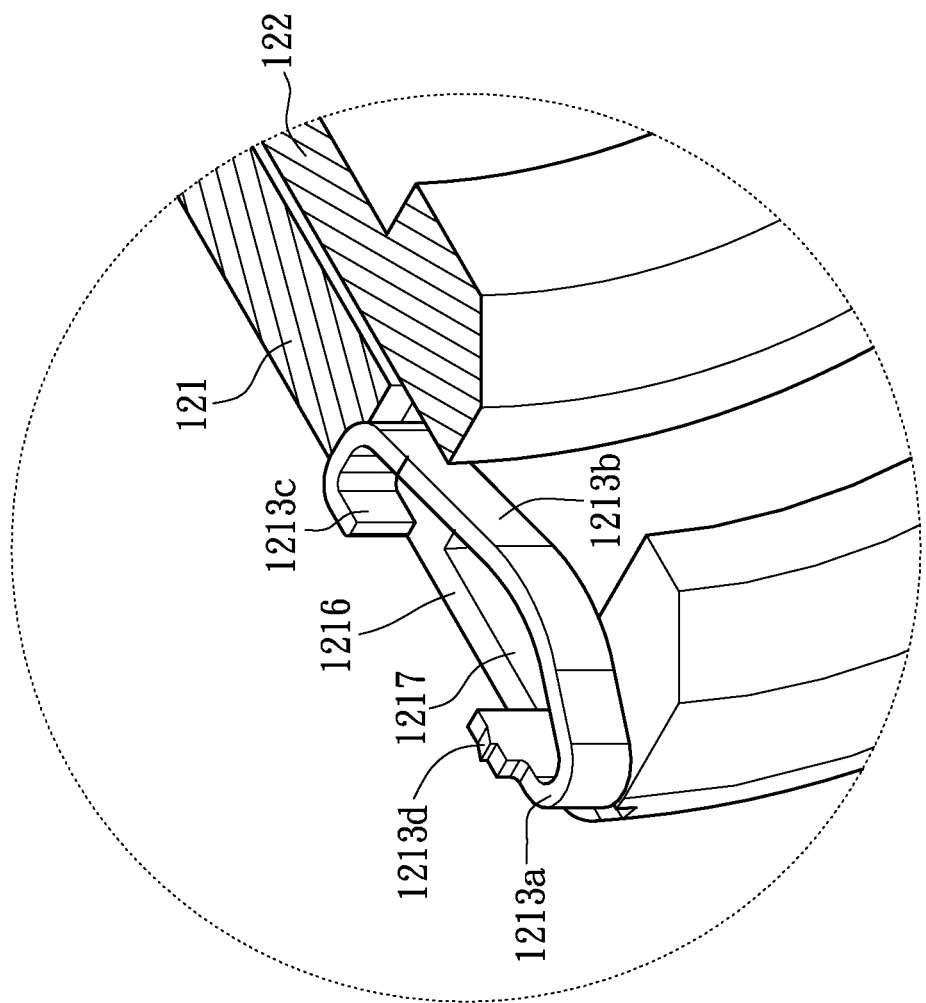
FIG. 1A is an enlarged view of circle A in FIG. 1.

Referring to FIGS. 1 and 1A, the front end of the plug shell 121 is formed with a groove 1216 for receiving the resilient positioning member 1213. The resilient positioning member 1213 may be a metallic resilient sheet or a plastic resilient sheet and its quantity may be two or more. The instant disclosure is not limited to the instant embodiment. In the instant embodiment, two resilient positioning members 1213 are disposed on the front end of the plug shell 121. It should be understood that any flexible structure providing similar function can be used to replace the resilient positioning member 1213. FIG. 1A shows an enlarged view of circle A in FIG. 1. In the instant embodiment, the resilient positioning member 1213 resembles "C". The resilient positioning member 1213 has a grapping portion 1213$a$, a connecting portion 1213$b$ and a positioning portion 1213$c$. The gripping portion 1213$a$ and the positioning portion 1213$c$ resemble the two ends of the letter "C", directing toward each other.

It is worth noting that the groove 1216 is further depressed to form a rail 1217 extending toward the bottom end of the groove 1216. The grapping portion 1213$a$ has a protrusion 1213$d$ conforming to the rail 1217 such that the resilient positioning member 1213 can be firmly engaged with the rail 1217. The positioning portion 1213$c$ of the resilient positioning member 1213 is suspended above the rear end of 1216 and the front end of the snap-fit portion 122.

Referring to FIGS. 2, 3 and 4A, the pluggable self-locking connector 1 further includes a cable clip 124 and a tail nut 125 sleeving the cable clip 124. The cable clip 124 is fastened to the rear end of the snap-fit portion 122 and connected to the plastic plug core 123 thereof. The interior of the tail nut 125 is formed with a set of inner thread 1251 conforming to a set of outer thread 1224 on the rear outer face of the snap-fit portion 122. As shown in FIG. 4A, in practice, a cable providing power (not shown) can be welded onto the plurality of pins 1121 of the plastic socket core 112, and the socket 11 is fastened by screws on the power supply equipment. Subsequently, another cable is welded to the outlet (not shown) of the plug pins 1231 of the plastic plug core 123. The cable clip 124 clamps, seals and fastens the assembly. Finally the tail nut 125 screws onto the snap-fit portion 122, and then the plug 12 and the socket 11 are ready to mate.

Please refer to FIGS. 4A to 8B showing the practical use of the pluggable self locking connector 1. FIG. 4A is a cross-sectional view along X axis showing the unassembled pluggable self locking connector. FIG. 4B is a cross-sectional view along Y axis showing the unassembled pluggable self locking connector. As shown in FIGS. 4A and 4B, the pair of resilient ribs 1221 formed on the snap-fit portion 122 increases the stability between the plug 12 and the socket 11 in combination. Before the combination of the plug 12 and the socket 11, the pair of resilient ribs 1221 of the snap-fit portion 122 is exposed from the corresponding openings 1211 on the plug shell 121. The second guiding faces 1221a of the two resilient ribs 1221 abut the rear end of the openings 1211 of the plug shell 121, and the snap-fit portion 122 is located at a first position.

Figure 5A:
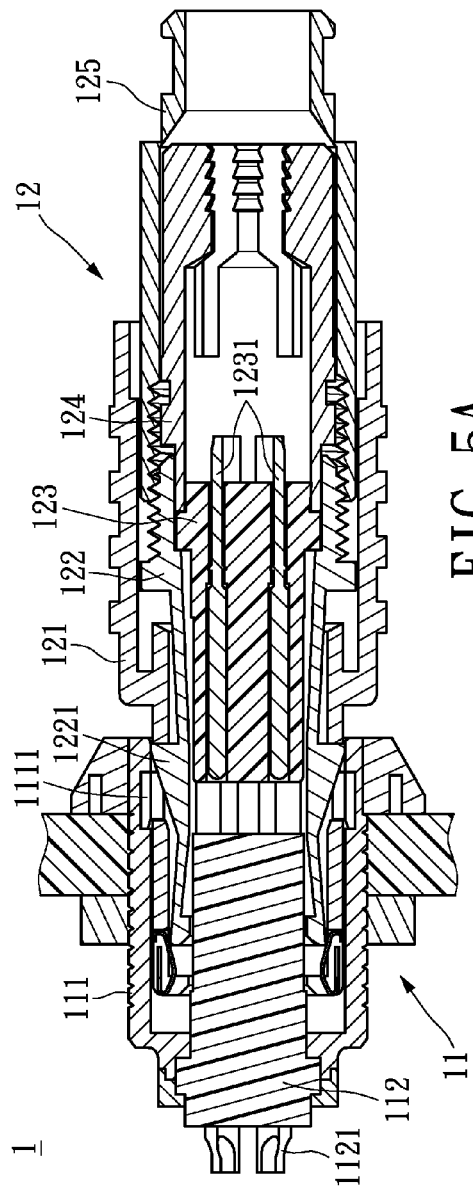
FIG. 5A is a cross-sectional view along X axis showing a pluggable self locking connector of the instant disclosure after insertion.
Figure 5B:
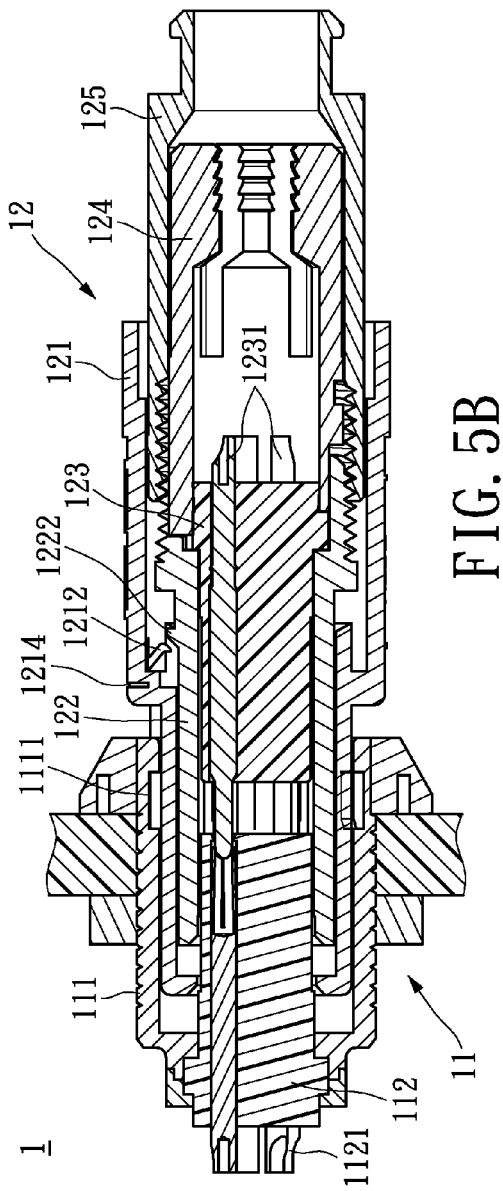
FIG. 5B is a cross-sectional view along Y axis showing a pluggable self locking connector of the instant disclosure after insertion.

Please refer to FIGS. 5 and 5B. FIG. 5A is a cross-sectional view along X axis showing the pluggable self locking connector during insertion. FIG. 5B is a cross-sectional view along Y axis showing the pluggable self locking connector after insertion. As shown in FIG. 5A, when the plug 12 and the socket 11 mate, the two resilient ribs 1221 are pressed by the socket case 111, and consequently the two resilient ribs 1221 retreat toward the interior of the plug shell 121 within the openings 1211. At the same time, the entire snap-fit portion 122 is slightly shrunk inwardly, causing a minor shift. As shown in FIG. 5B, at the time the resilient latch 1212 of the plug shell 121 is not engaged with the bump 1222 of the snap-fit portion 122.

Please refer to FIGS. 6A and 6B. FIG. 6A is a cross-sectional view along X axis showing the pluggable self locking connector being locked after insertion. FIG. 6B is a cross-sectional view along Y axis showing the pluggable self locking connector being locked after insertion. As shown in FIG. 6A, the depression 1111 of the socket case 111 is positioned to receive the two resilient ribs 1221 of the snap-fit portion 122. Hence, when the plug 12 and the socket 11 mate, the two resilient ribs 1221 return to the relaxed state before being compressed and rest in the depression 1111 of the socket case 111. Meanwhile, the overall configuration of the snap-fit portion 122 returns to an uncompressed state. The plug 12 and the socket 11 are then electrically conducted. As shown in FIG. 6B, the resilient latch 1212 of the plug shell 121 and the bump 1222 of the snap-fit portion 122 are not engaged.

Please refer to FIGS. 7A and 7B. FIG. 7A is a cross-sectional view along X axis showing the pluggable self locking connector being withdrawn after insertion. FIG. 7B is a cross-sectional view along Y axis showing the pluggable self locking connector being withdrawn after insertion. As shown in FIG. 7A, the plug 12 and the socket 11 are to be parted. The first guiding face 1111a of the depression 1111 of the socket case 111 abuts the second guiding face 1221a of the resilient rib 1221, and therefore the snap-fit portion 122 is confined to a still. However, when the plug 12 is removed from the socket 11, the second guiding face 1221a of the resilient rib 1221 of the snap-fit portion 122 moves from the rear to the front end of the opening 1211 of the plug shell 121. As a result, the snap-fit portion 122 is located at a second position. At the present time, as shown in FIG. 7B, the resilient latch 1212 of the plug shell 121 and the bump 1222 of the snap-fit portion 122 are tightly engaged. Therefore the snap-fit portion 122 is confined to the second position and cannot return to the first position (shown in FIG. 2). In addition, the plug shell 121 slides along the round curve A2 of the resilient rib 1221 to the guiding slope 1221b. Consequently, the resilient ribs 1221 retract into the plug shell 121 and exit the depression 1111 of the socket case 111. The plug 12 is then smoothly pulled out from the socket case 111.

When the second guiding face 1221a moves from the rear to the front end of the opening 1211, the front end of the snap-fit portion 122 presses against the connecting portion 1213b of the resilient positioning member 1213, such that the positioning portion 1213c of the resilient positioning member 1213 abuts the rear end of the groove 1216 and shifts upwards. As a result, the front end of the positioning portion 1213c is exposed on the plug shell 121 (as shown in FIG. 8A). It is worth noting that because the resilient latch 1212 of the plug shell 121 are engaged with the bump 1222 of the snap-fit portion 122, the front end of the snap-fit portion 122 firmly presses against the resilient positioning members 1213. In this regard, the resilient positioning members 1213 are firmly exposed on the plug shell 121.

Please refer to FIGS. 8A and 8B. FIG. 8A is a cross-sectional view along X axis showing the pluggable self locking connector after second insertion. FIG. 8B is a cross-sectional view along Y axis showing the pluggable self locking connector after second insertion. As shown in FIG. 8A, when the plug 12 rejoins the socket 11, the front end of the positioning portion 1213c of the resilient positioning member 1213 is completely exposed on the plug shell 121. Hence, the front ends of the two resilient positioning members 1213 abut the socket case 111 and the plug 12 cannot be completely inserted to the socket case 111 for electrical connection. In other words, the pluggable self locking connector 1 can prevent repeated plugging/insertion, therefore avoiding pathogen spreading. As shown in FIG. 8B, the resilient latch 1212 of the plug shell 121 and the bump 1222 of the snap-fit portion 122 are tightly engaged.

Figure 9:
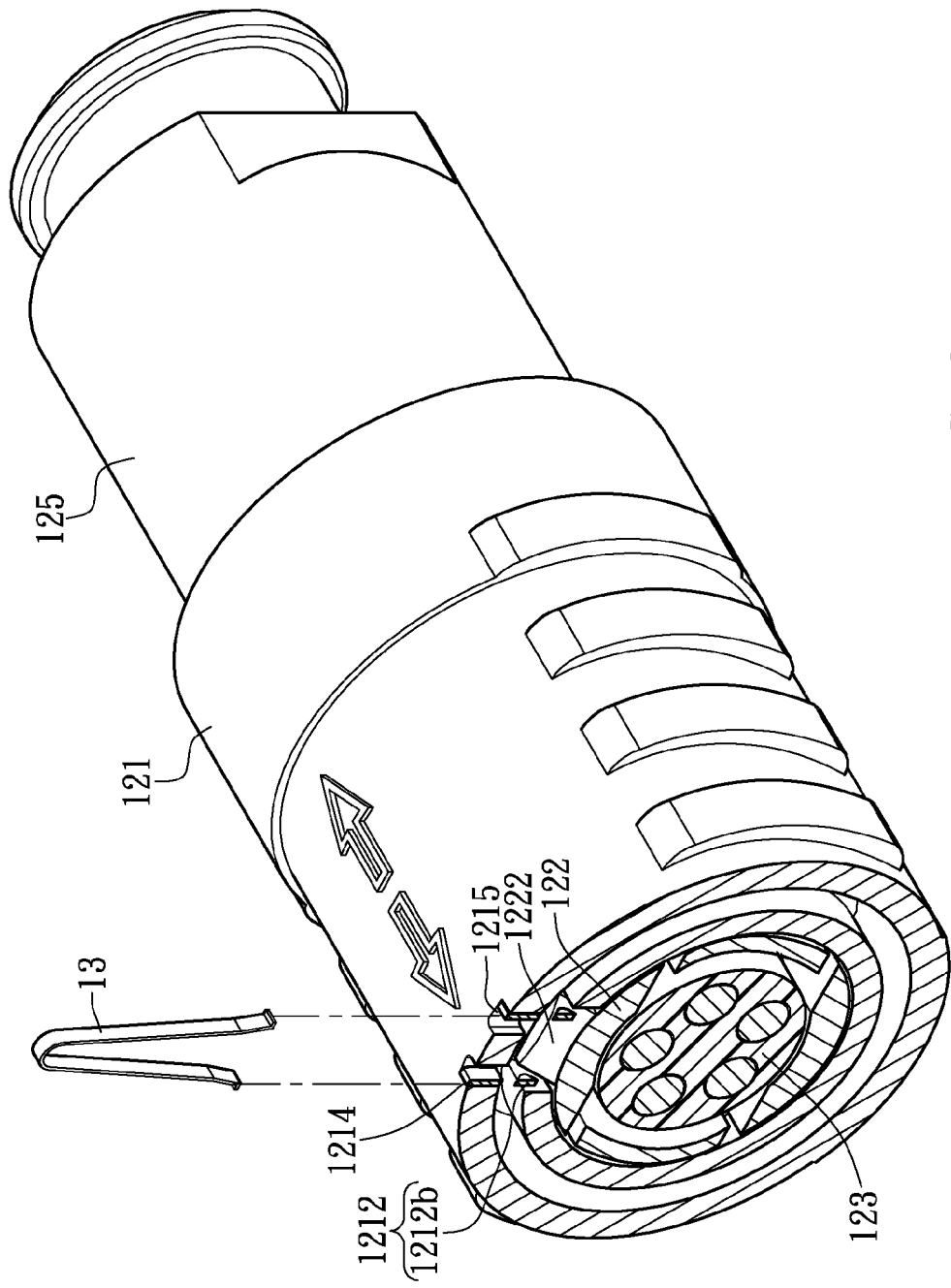
FIG. 9 is a cross-sectional perspective view of a pluggable self locking connector of the instant disclosure during maintenance.
Figure 10:
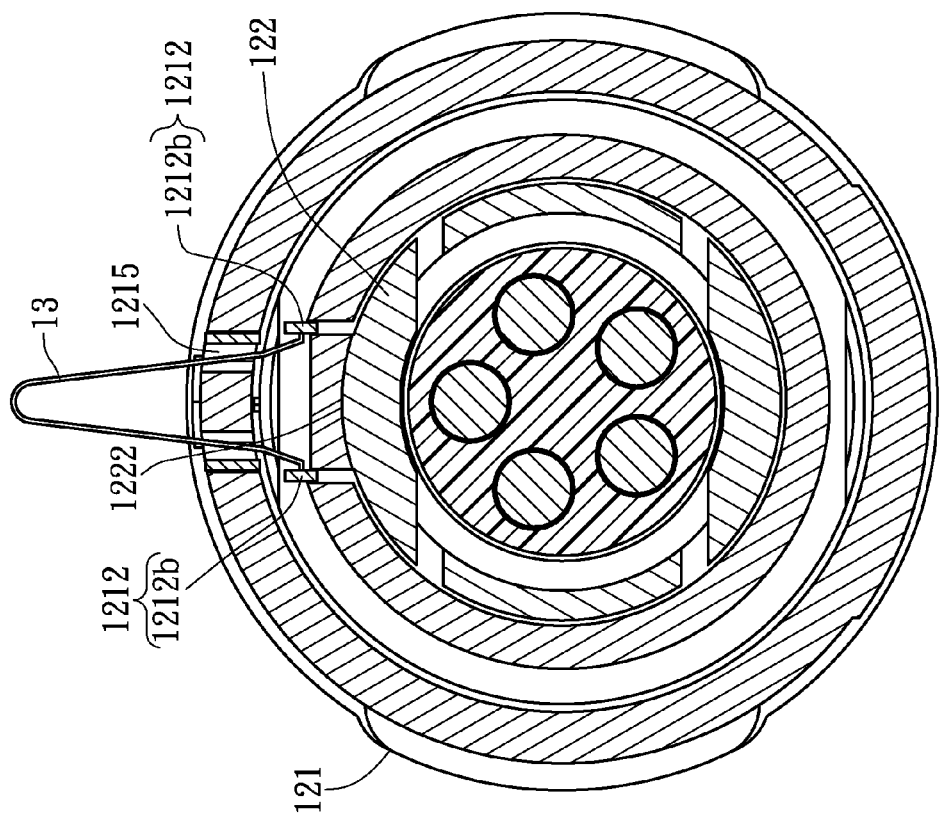
FIG. 10 is a cross-sectional view of a pluggable self locking connector of the instant disclosure during maintenance.

Please refer to FIGS. 9 and 10. FIG. 9 is a cross-sectional perspective view of the pluggable self locking connector during maintenance. FIG. 10 is a cross-sectional view of the pluggable self locking connector during maintenance. As shown in FIG. 9, the pluggable self locking connector 1 further includes a resilient maintenance clip 13 resembling a horse shoe. The rear ends of the latch slots 1214 of the plug shell 121 further extend to form two maintenance openings 1215. When conducting the maintenance of the pluggable self locking connector 1, as shown in FIG. 10, the resilient maintenance clip 13 is inserted to the maintenance openings 1215 and abuts the hooks 1212b. When the hooks 1212b are pushed, they fall off from the bump 1222 of the snap-fit portion 122 (shown in FIG. 8B) such that the snap-fit portion 122 returns from the second position to the first position (shown in FIG. 4A).

It should be understood that any orientation used in the description is for reference only and the instant disclosure is not limited thereto.

In summary, the socket and plug of the pluggable self locking connector are tightly engaged because the depression of the socket case and the resilient ribs of the snap-fit portion fittingly match. The snap-fit portion is confined by the socket case, and therefore the resilient latch of the plug shell and the bump of the snap-fit portion restrict the position of each other. Also, the resilient positioning member blocks reentry to the socket case such that the plug cannot rejoin with the socket. The avoidance of secondary entry can effectively reduce the rate of instrument-related pathogen infection. The round angle of the resilient rib of the snap-fit portion creates smooth sliding when the plug shell presses the resilient rib into the interior thereof. That is to say, the plug can be easily removed from the socket case. Because the resilient latch of the plug shell and the bump of the snap-fit portion are engaged, the front end of the snap-fit portion firmly presses the resilient positioning member and therefore a portion of the resilient positioning member is exposed outside the plug shell.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. A pluggable self locking connector comprising:
a socket including a socket case, the socket case including a plastic socket core having a plurality of socket pins in an interior and a depression on an inner wall thereof; and
a plug including a plug shell and a snap fit portion slidably coupled to the plug shell, the plug coupled to the socket case and connected thereto, the snap fit portion having a plastic plug core formed with a plurality of plug pins corresponding to the socket pins, an outer wall of the snap fit portion being formed with at least one deformable resilient rib and a bump, the plug shell being formed with an opening for slidably receiving the resilient rib and a resilient latch corresponding to the bump, and a front end of the plug shell having at least one resilient positioning member;
wherein when the socket and the plug mate, the resilient rib of the snap fit portion and the depression of the socket case mate, when the socket and the plug separate, the resilient rib is confined by the depression of the socket case and the resilient latch of the plug shell and the bump of the snap fit portion are tightly engaged; and a front end of the snap fit portion presses the resilient positioning member of the plug shell and a portion of the resilient positioning member is exposed outside the plug shell.

2. The pluggable self locking connector according to claim 1, wherein the outer wall of the snap fit portion is formed with a plurality of slits and the resilient ribs are located between the slits.

3. The pluggable self locking connector according to claim 2, wherein a gap is formed between the snap fit portion and the plastic plug core, allowing the resilient rib for retracting thereto.

4. The pluggable self locking connector according to claim 3, wherein the inner wall of the depression is formed with a first guiding face, and the resilient rib has a second guiding face corresponding to the first guiding face.

5. The pluggable self locking connector according to claim 4, wherein the outer face of the resilient rib is formed with a guiding slope connecting to the second guiding face, the second guiding face and the guiding slope form an angle there-between, and the front end of the guiding slope is curved.

6. The pluggable self locking connector according to claim 5, wherein a middle portion of the plug shell is formed with a latch slot for receiving the resilient latch, the resilient latch has a main body resembling a horse shoe and two parallel hooks slantingly extending from the main body, and the two hooks and the bump of the snap fit portion are engaged.

7. The pluggable self locking connector according to claim 6, wherein the main body is formed with a pair of trenches conforming to the contours of the hooks for receiving the hooks therein.

8. The pluggable self locking connector according to claim 7, wherein the latch slot further extends to form two maintenance openings.

9. The pluggable self locking connector according to claim 8 further including a resilient maintenance clip resembling a horse shoe, two ends of the resilient maintenance clip respectively inserting to the two maintenance openings and abutting the two hooks.

10. The pluggable self locking connector according to claim 5, wherein the resilient positioning member has a grapping portion, a connecting portion and a positioning portion, one end of the connecting portion bends toward the rear end of the plug to form the grapping portion and the other end thereof bends toward the front end of the plug to form the positioning portion.

11. The pluggable self locking connector according to claim 10, wherein the plug shell is formed with a groove in conformity with the resilient positioning member, the inner wall of the groove is depressed to formed a rail, the grapping portion has a protrusion in cooperation with the rail, and the positioning portion is suspended proximate to the rear end of the groove.

12. The pluggable self locking connector according to claim 1 further comprising a cable clip and a tail nut sleeving the cable clip, the cable clip coupled to the rear end of the snap fit portion, an inner wall of the tail nut formed with a set of inner thread and an outer face of a rear end of the snap fit portion formed with a set of outer thread corresponding to the inner thread.

* * * * *